United States Patent [19]

Lebkowski et al.

[11] Patent Number: 5,173,414

[45] Date of Patent: Dec. 22, 1992

[54] PRODUCTION OF RECOMBINANT ADENO-ASSOCIATED VIRUS VECTORS

[75] Inventors: Jane S. Lebkowski, Portola Valley; Maureen A. McNally; Thomas B. Okarma, both of Palo Alto, all of Calif.

[73] Assignee: Applied Immune Sciences, Inc., Menlo Park, Calif.

[21] Appl. No.: 605,775

[22] Filed: Oct. 30, 1990

[51] Int. Cl.$^5$ ............... C12N 15/64; C12N 15/85; C12N 15/86; C12N 15/65

[52] U.S. Cl. .............. 435/172.3; 435/320.1; 935/27; 935/32; 935/56; 935/57

[58] Field of Search ............ 435/320.1, 172.3, 235.1, 435/69.1; 935/32, 34, 57, 27, 56

[56] References Cited

U.S. PATENT DOCUMENTS 4,686,186  8/1987  Sugden ..................... 435/320.1 X
4,797,368  1/1989  Carter et al. ................ 435/320.1

OTHER PUBLICATIONS

Clemens, D. L. et al. 1989, *J. Virol.* vol. 63 pp. 2737–2745.
Mendelson, E. et al. 1988, *Virology*, vol. 166 pp. 154–165.
Samulski, R. J. et al. 1989, *J. Virol.* vol. 63 pp. 3822–3828.
Stary, A. et al. 1989, *J. Virol.* vol. 63, pp. 3837–3843.
Berns and Bohensky, "Adeno-Associated Viruses: An Update", *Advances in Virus Research*, (1972) (Academic Press), 32:243–306.
Laughlin et al., *Gene* (1983) 23:65–73.
Beaton et al., *J. Virol.* (1989) 63:4450–4454.
Tratschin et al., *Mol. Cell Biol.* (1984) 4:2072–2081.
Hermonat and Muzyczka, *Proc. Natl. Acad. Sci. USA* (1984) 4:2072–2081.
McLaughlin et al., *J. Virol.* (1988) 62:1963–1973.
Lebkowski et al., *Mol. Cell Biol.* (1988) 3988–3996.

*Primary Examiner*—Richard A. Schwartz
*Assistant Examiner*—Mary E. Mosher
*Attorney, Agent, or Firm*—Morrison & Foerster

[57] ABSTRACT

A simplified method to produce recombinant adeno-associated virus (AAV) vectors is described. The procedure involves the use of chimeric plasmids which incorporate the Epstein Barr nuclear antigen (EBNA) gene, the latent origin of replication of Epstein Barr Virus (oriP), and a recombinant AAV genome. The chimeric plasmids themselves are also a part of the present invention. These EBV/AAV plasmids are maintained as multicopy extra-chromosomal elements in cells, such as human 293 cells. Permanent cell lines carrying these EBV/AAV plasmids are induced to produce large amounts of recombinant AAV virus upon addition of wild-type, adeno-associated virus helper functions. Recombinant AAV vectors produced in this manner are capable of transducing exogenous genes into other human cell lines and exhibit all of the attributes of viral elements produced by conventional methods.

9 Claims, 1 Drawing Sheet

PRODUCTION OF RECOMBINANT ADENO-ASSOCIATED VIRUS VECTORS

INTRODUCTION

1. Technical Field

The present invention is directed generally to the field of genetic engineering and is particularly directed to the production of recombinant adeno-associated virus (AAV) vectors for use in transducing exogenous genes into human cell lines.

2. Background

Adeno-associated virus (AAV) is a single-stranded DNA parvovirus which is endogenous to the human population. Although capable of productive infection in cells from a variety of species, AAV is a dependovirus, requiring helper functions from either adenovirus or herpes virus for its own replication. In the absence of either of these helper viruses, AAV will infect cells, uncoat in the nucleus, and integrate its genome into the host chromosome, but will not replicate or produce new viral particles.

The genome of AAV has been cloned into bacterial plasmids and is well characterized. The viral genome consists of 4682 bases which include two terminal repeats of 145 bases each. These terminal repeats serve as origins of DNA replication for the virus. Some investigators have also proposed that they have enhancer functions. The rest of the genome is divided into two functional domains. The left portion of the genome codes for the rep functions which regulate viral DNA replication and viral gene expression. The right side of the viral genome contains the genes for the structural capsid proteins VP1, VP2 and VP3. Both the rep and capsid proteins of AAV function in trans during productive viral replication.

AAV virus is considered an ideal candidate for use as a transducing vector, and it has been used in this manner. Recombinant AAV viruses have been constructed in a number of laboratories and have been used to carry exogenous genes into cells of a variety of lineages. In these vectors, the capsid and/or rep genes of AAV are deleted from the viral genome and replaced with a DNA segment of choice. Current vectors can accommodate up to 4300 bases of desired DNA. To make a recombinant virus, plasmids containing the desired viral construct are transfected into adenovirus-infected cells. In addition, a second helper plasmid is cotransfected into these cells to provide the AAV rep and capsid functions which are obligatory for replication and packaging of the recombinant viral construct. Under these conditions, the rep and capsid proteins of AAV act in trans to stimulate replication and packaging of the recombinant AAV construct. Three days after transfection, recombinant AAV virus is harvested from the cells along with adenovirus. The contaminating adenovirus is then inactivated by heat treatment.

Although the individual procedures used to make recombinant AAV vectors are relatively simple, the process suffers two drawbacks. Repeated transfection with the recombinant AAV plasmid is required each time recombinant virus is to be made. Moreover, the production of recombinant virus is relatively inefficient due to the inherent inefficiency of cotransfecting two plasmids into a large proportion of cells. Accordingly, new procedures for the production of recombinant AAV vectors are highly desirable.

Relevant Literature

For a general review of adeno-associated viruses, see Berns, K. I., and R. A. Bohensky (1987), "Adeno-Associated Viruses: An Update," in Advances in Virus Research, Vol. 32. Academic Press. 32:243–306. The genome of AAV is described in Laughlin, C. A., et al., (1983) "Cloning of infectious adeno-associated virus genomes in bacterial plasmids," Gene 23:65–73. Expression of AAV is described in Beaton, A., et al., (1989) "Expression from the Adeno-associated virus p5 and p19 promoters is negatively regulated in trans by the rep protein," J. Virol. 63:4450–4454. Construction of recombinant AAV viruses is described in a number of publications: Tratschin, J. D., et al., (1984) "Adeno-associated virus vector for high frequency integration, expression and rescue of genes in mammalian cells," Mol. Cell. Biol. 4:2072–2081; Hermonat, P. L., and N. Muzyczka (1984) "Use of adeno-associated virus as a mammalian DNA cloning vector: Transduction of neomycin resistance into mammalian tissue culture cells," Proc. Natl. Acad. Sci. USA 81:6466–6470; McLaughlin, S. K., et al., (1988) "Adeno-associated virus general transduction vectors: Analysis of Proviral Structures," J. Virol. 62:1963–1973; and Samulski, R. J., et al., (1989) "Helper-free stocks of recombinant adeno-associated viruses: normal integration does not require viral gene expression," J. Virol. 63:3822–3828. Cell lines that can be transformed by recombinant AAV viruses are described in Lebkowski, J. S., et al., (1988) "Adeno-associated virus: a vector system for efficient introduction and integration of DNA into a variety of mammalian cell types," Mol. Cell. Biol. 8:3988–3996.

SUMMARY OF THE INVENTION

It is an object of the present invention to provide techniques and genetic constructs useful for producing AAV recombinant vectors conveniently and in large quantities.

These and other objects of the invention as will hereinafter become more readily apparent have been accomplished by providing a method of cloning a preformed AAV vector containing exogenous genetic material into an Epstein Barr virus (EBV) plasmid, wherein said EBV plasmid comprises in the 5'-3' direction a gene for the Epstein Barr virus nuclear antigen (EBNA), an EBV oriP DNA segment, and a preformed AAV vector containing exogenous genetic material. Other genetic information, such as a detectable genetic marker, can be present in the EBV plasmid. The composite plasmid is transfected into a host cell line which is then grown in a cell growth medium, the AAV vector being multiplied during this phase as a result of cell growth. After an appropriate period of time, the transfected host cell is contacted with a source of adenovirus or herpes virus helper functions (in the form of complete viruses or otherwise) and with sufficient genetic information to provide the missing replication functions (capsid and/or rep regions of the AAV virus). The desired AAV vector containing exogenous genetic material is then isolated from the cell growth medium.

In addition to the method described above, the present invention also includes certain genetic constructs that are used in the practice of the invention.

BRIEF DESCRIPTION OF THE DRAWINGS

The present invention will be better understood by reference to the following detailed description of specific embodiments when considered in combination with the drawings that form part of the present specification, wherein:

The FIGURE is a schematic diagram of a number of plasmids that are either constructs of the invention or that are used to form constructs of the invention. In each case, the schematic maps are drawn to scale, with the restriction sites denoted in the poly linker not necessarily representing single cloning sites.

DESCRIPTION OF THE SPECIFIC EMBODIMENTS

Figure 1:
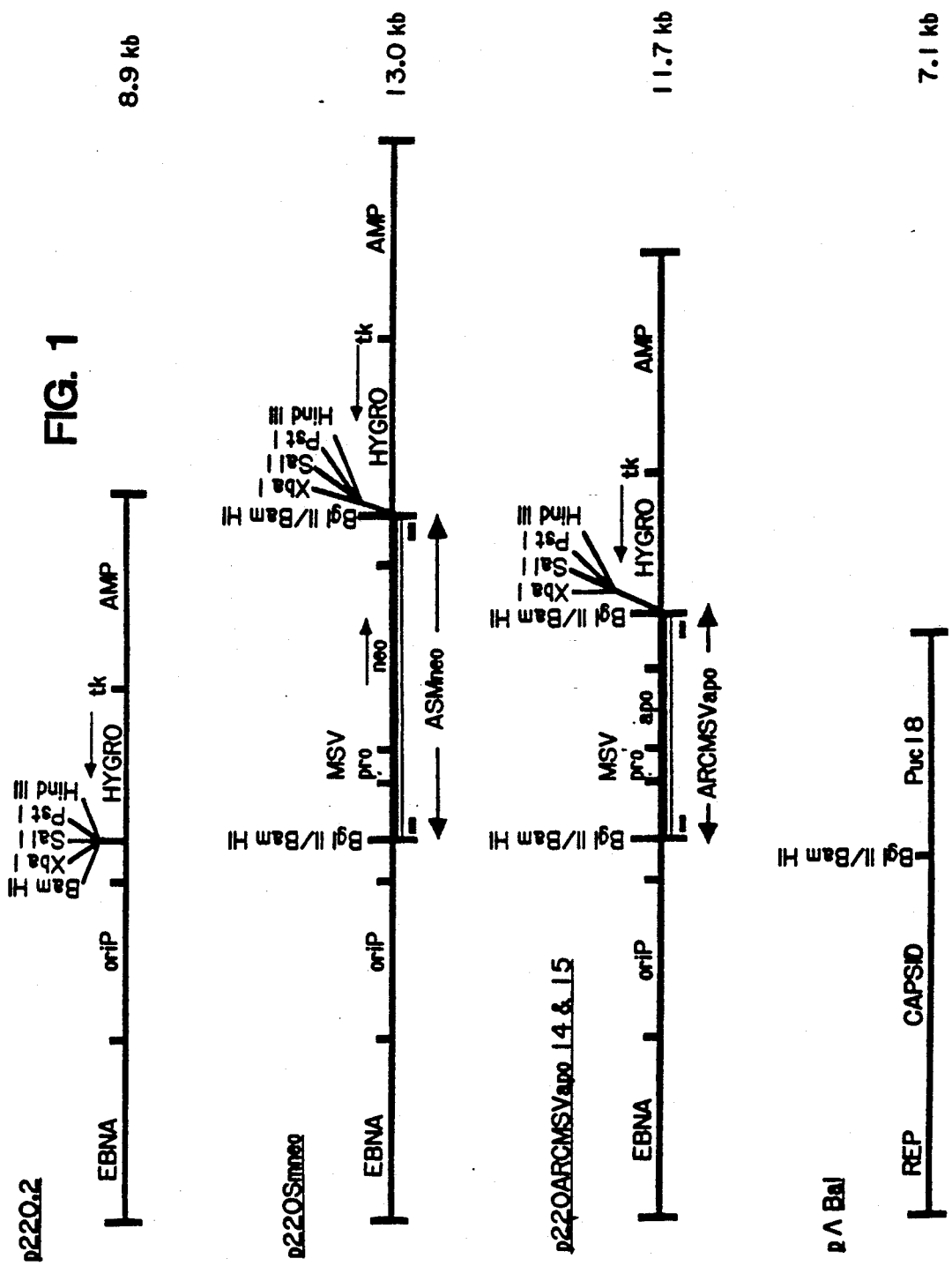

The present invention includes a new system to produce large amounts of recombinant adeno-associated virus (AAV) vectors. The constructs used in the practice of the invention rely in part on properties of Epstein Barr virus (EBV) plasmids, which in the presence of the EBV nuclear antigen (EBNA) remain as autonomously replicating plasmids in human cells. Although amplification of viral sequences using EBV vectors has previously been described, EBV plasmids have not been used in any system that generates a second virus vector, in this case the recombinant AAV vector. Furthermore, there was no indication whether constructs containing characteristics from both EBV vectors and AAV vectors would retain their desirable properties during cell reproduction or lytic production of virus.

In the procedure of the present invention, multiple copies of a recombinant AAV genome are permanently established in human cells as part of a chimeric AAV-/EBV plasmid. To produce large amounts of recombinant AAV virus, these cells are infected with adenovirus or herpes virus (or appropriate recombinant constructs containing the required helper functions) and transfected with plasmids encoding any missing wild-type AAV rep or capsid functions. Under these circumstances, lytic AAV replication ensues, and the amplified genomes are packaged as viable transducing vectors.

The method of the invention of producing recombinant AAV vectors offers several advantages over conventional procedures for producing recombinant adeno-associated virus. Using the system of the invention, permanent cell lines containing a cloned recombinant AAV genome are constructed. These cell lines may be used continually as a stable source of recombinant virus obviating the need for relatively inefficient plasmid cotransfections every time recombinant AAV virus is to be made. Furthermore, recombinant EBV plasmids, once established in host cells, are stable structurally for at least three months, and lines containing intact copies of the chimeric plasmid can be screened. Newly transfected DNA, on the other hand, suffers a very high rate of point and rearrangement mutations, and viral production systems which rely on repeated transfection of recombinant virus genomes typically have a high frequency of mutant virus. This consideration is especially important if a recombinant virus is to be used in vivo in gene therapy protocols.

The present invention uses a chimeric AAV/EBV plasmid to maintain recombinant AAV genomes at high copy number in a cell line permissive for efficient AAV reproduction; i.e., a good host for EBV plasmid vectors. This is in contrast to several studies which previously have reported that multiple copies of wild type or recombinant AAV virus integrate as tandem arrays into a fraction of infected Detroit 6 cells. See, Cheung, A. K., et al., "Integration of the Adeno-Associated Virus Genome into Cellular DNA in Latently Infected Human Detroit 6 Cells," J. Virol. 33:739-748. The integrated virus can be "rescued" from Detroit 6 cells upon adenovirus infection. Such a system could also be used as the starting point for the generation of recombinant AAV virus. However, the present inventors have not observed tandem integration of AAV in host cells, such as human 293 cells, that are more useful in large-scale virus production. Only single copies of recombinant virus were observed in such cells, and viral "rescue" upon adenovirus superinfection was rarely seen. Therefore, the AAV/EBV chimeric vector system is more suitable for large scale applications. With the system of the invention, production of cell clones containing multiple intact copies of the plasmid is efficient. Moreover, it allows the use of host cells, such as 293 cells, which are easily of transfected and expressed and which produce large quantities of virus. While integration is possible, integrated vectors represent a less preferred aspect of the invention.

The original AAV/EBV chimeric vectors used in the development of the present invention contained recombinant AAV genomes which were wild type for the viral rep proteins. In every case tested, these vectors failed to remain as plasmids in host cells, regardless of the orientation of the AAV construct within the EBV vector. Plasmid maintenance was only obtained when the wild-type rep functions were eliminated from the recombinant AAV genome. In the presence of wild-type rep genes, the genes themselves or their encoded proteins appear to have initiated EBV plasmid replication. Alternatively, they may have interfered with the expression of the EBNA functions encoded on the plasmid which are essential for plasmid maintenance. Such negative regulation of gene expression has been observed previously for other systems. Accordingly, the AAV vector portions of the genetic constructs of the invention are missing all or portions of either the rep or capsid protein genes.

Recombinant virus produced using the AAV/EBV chimeric plasmids of the invention has the capability of transducing genes with high frequency into human cells. In addition, these stocks have undetectable levels of contaminating wild-type AAV virus. Although the methods described here generate stocks with high levels of recombinant virus, higher levels are theoretically possible. As described here, the system still provides for only the transient expression of AAV rep and capsid genes in order to supply needed wild type AAV functions. This situation can be optimized for the production of AAV capsid proteins which are required stoichiometrically for the production of recombinant virus.

The method of invention can be carried out with a wide variety of host cells, generally any human cell that can be infected by an Epstein Barr virus. Host cell lines are generally selected for ease of growth without complex media requirements, ease of drug selection of clones, high cloning efficiency, and maintenance of the highest possible EBV-AAV chimeric plasmid copy number. Example cell lines include 293, HeLa, KB and JW-2 cells. These cell lines are commonly available; for example, 293 cells, HeLa cells and KB cells are commercially available through the American Type Culture Collection (e.g., 293 cells, which are transformed primary human embryonal kidney cells, are available under the accession number ATCC CRL 1573).

Preparation of a recombinant AAV vector is well understood by those skilled in the art. The principal differences between previous vectors that have been produced and AAV vectors used in the practice of the present invention is that the AAV vectors of the invention lack a functioning rep genetic region. As previously discussed, this is the region of the AAV genome that codes for the rep functions which regulate viral DNA replication and viral gene expression.

Various techniques exist for eliminating a functioning rep genetic region. Examples of typical genetic manipulations include deletions of genetic material in this region, insertions of genetic material that causes reading frame errors in this region, and point mutations that disrupt the replication function. Any AAV vector system can readily be tested for a functioning rep region by transfecting the construct into adenovirus-infected cells and examining their extracts 48 hours later for the presence of replicating vector genomes. If a wild-type gene is present, replicating DNA will be apparent on Southern blots.

There are relatively few limitations on the recombinant AAV vector. The complete AAV genome should not exceed 4700 base pairs. The two terminal repeats (origins of replication) of AAV must be present in the recombinant AAV construct. There is no limitation on the exogenous genetic material that is included in the recombinant plasmid vector.

The recombinant plasmid vector of the invention contains, in addition to the recombinant adeno-associated virus vector, sufficient genetic material derive from the Epstein Barr virus to allow the recombinant plasmid to function in the manner described herein. Minimally, this includes a genetic region encoding an Epstein Barr nuclear antigen and an Epstein Barr latent origin of replication, generally referred to as the oriP region. Other regions of an Epstein Barr virus can be present, but are not required.

The individual steps of the present invention used in transfecting cells with the recombinant plasmid of the invention are conventional and have previously been described for transforming cells with Epstein Barr virus. Likewise, the process of growing transfected cells in a cell growth medium is conventional. Once cells have reproduced to the desired level, the host cells are infected with adenovirus or herpes virus, typically in the form of a complete adenovirus or herpes virus, and transfected with a plasmid or other vector containing wild-type adeno-associated virus helper functions.

As previously indicated, AAV is a dependovirus, requiring helper functions from either adeno-virus or herpes virus for its own replication. In the process of the invention, helper viruses are generally provided, namely either adeno-virus or herpes virus. However, it may also be possible to provide recombinant plasmids containing the helper functions. Such recombinant plasmids are not commercially available, but there is no reason to believe that use of such recombinant plasmids would not work equally as well as providing helper functions in the form of an adenovirus or herpes virus.

Additionally, it is necessary to provide any missing AAV proteins, such as rep or capsid proteins, that have been deleted from the AAV recombinant vector. This is typically done by transfecting the host cell line with a plasmid containing the appropriate genetic material.

Specific examples of the individual steps described above are set forth in the following examples. However, it will be apparent to one of ordinary skill in the art that many modifications can be made, and that the examples are provided for purposes of illustration only and are not limiting of the invention unless so specified.

EXAMPLE 1

Plasmid Constructions

All DNA manipulations and plasmid constructions were performed using standard procedures. The plasmid p Bal was constructed as described by Lebkowski et al., op. cit. We cloned two different recombinant AAV constructs into the EBV plasmid p220.2, as shown in the FIGURE. Plasmid p220.2 contains the gene for the Epstein Barr virus nuclear antigen (EBNA) and the viral oriP DNA fragment which serves as the latent origin of replication of the virus (Yates, J. L., et al., "Stable Replication of Plasmids Derived from Epstein-Barr Virus in Various Mammalian Cells," Nature 313:812–815 and Sugden, B., et al., "A Vector That Replicates as a Plasmid and Can Be Efficiently Selected in B-lymphoblasts Transformed by Epstein-Barr Virus," Mol. Cell. Biol. 5:410–413). The plasmid also contains the hygromycin B resistance gene to allow selection in mammalian cells. When p220.2 is transfected into a number of human cell lines, hygromycin resistant transformants can be selected with high frequency. In these drug resistent cells, p220.2 is maintained as a autonomously replicating unit at approximately 10–100 copies per cell.

The chimeric AAV/EBV vector constructions are shown in the FIGURE. p220ASMneo was constructed by inserting the partial BGlII fragment from pSMneo, an exemplary, previously known, recombinant AAV vector, into the BamHI polylinker site of p220.2. Likewise, the recombinant AAV vector ARCMSVapo was cloned into p220.2 to form p220ARCMSVapo 14 and 15. Subclones 14 and 15 denote the two different orientations of ARCMSVapo in p220.2.

To construct p220ARCMSVapo 14 and 15, pARCMSVapo was used as an intermediate. Briefly, pARCMSVapo was constructed by inserting into pASHK a HindIII-KpnI fragment containing an apo Al cDNA clone. The Murine sarcoma virus LTR was then inserted into the HindIII site of this plasmid yielding pARCMSVapo. To construct p220ARCMSVapo, the recombinant AAV vector was cleaved from pARCMSVapo with BglII and inserted into the BamHI site of p220.0.

EXAMPLE 2

Cells: growth and maintenance

Human 293 cells, available from the ATCC as CRL 1573, were maintained in Dulbecco's modified Eagle's medium (DMEM) containing 10% fetal calf serum and 100 U/ml penicillin and streptomycin. Cell were grown in a humidified 37 degree incubator supplemented with 5% $CO_2$. Selection of Hygromycin B resistant 293 cells usually started 3–5 days after transfection with AAV-/EBV chimeric plasmids. To start the selection process, the culture medium was withdrawn from the cells and fresh medium containing either 200 µg/ml hygromycin B or 1 mg/ml G418 was added. The procedure was repeated every 2–3 days until the selection process was complete. 293 cells containing chimeric AAV/EBV plasmids were constantly maintained in culture medium containing the appropriate selective drug.

K562 cells were grown in RPMI containing 10% Fetal calf serum and 100 U/ml penicillin and streptomycin. K562 cells were infected with recombinant AAV stocks as described by Lebkowski et al., op. cit., except that $1 \times 10^6$ K562 cells were incubated with 5 ml of any given viral stock. Viral infection efficiencies were determined by monitoring G418 resistance frequencies in the manner described by Lebkowski et al.

EXAMPLE 3

Transfection of Cells with Recombinant Plasmids and Evaluation of Transfected Cells.

All three AAV/EBV chimeric vectors were transfected into human 293 cells, and stable drug-resistant cell lines were selected. 293 cells containing 220ARCMSVapo 14 and 15 were selected in the presence of hygromycin B, whereas cells transformed by 220SMneo were selected using the drug G418. Individual drug-resistant clones containing each construct were grown to mass culture and used for experimentation. Pools of greater than 100 individual 293 cell clones were also made to represent a population of drug resistant clones. These pools are referred to as "populations."

Cells transformed by the three AAV/EBV constructs were examined for autonomously replicating chimeric plasmid. In these experiments, small molecular weight DNA was extracted from selected cell lines using the procedure of Hirt. The extracted DNA was introduced into E. coli strain HB101, and transformed bacteria were selected in the presence of ampicillin. Plasmid DNA was isolated from cultures inoculated with individual bacterial colonies and was characterized by restriction enzyme analysis on acrylamide gels.

Plasmid p220SMneo could be rescued from G418-resistant 293 cells and reintroduced into E. coli. The plasmid DNA that was isolated from individual bacterial colonies transformed with small molecular weight DNA from 7 individual and one population of p220SMneo 293 cell could be seen on the gels. At the time of Hirt extraction, these G418 resistant 293 cells had been in culture for over 2 months. In all instances, HindIII restriction analysis of the isolated plasmids yielded DNA fragments of the expected length of 0.5, 2.8 and 9.7 kb. Such results indicate that p220SMneo was maintained as a plasmid in the G418-resistant 293 cells. The rescued plasmids were also identical in size and restriction analysis to the original p220SMneo, suggesting that the plasmid did not undergo major rearrangements during its residence in the mammalian cells. These observations were verified by Southern blot analysis of HindIII-restricted, small molecular weight DNA isolated from the various G418-resistant 293 cells.

Similar analysis was performed on hygromycin-B-resistant 293 cell clones and populations that were generated using the plasmids p220ARCMSVapo14 and 15. As above, this analysis was performed on hygromycin-B-resistant 293 cells that had been in culture for over 2 months. The HindIII restriction digests of plasmid DNA isolated from bacterial colonies transformed by small molecular weight DNA from hygromycin-resistant 293 cells could be seen in the gels, as could the plasmid rescued from two p220ARCMSVapo15 293 cell clones. Again, in all of the cases, intact plasmid could be rescued from the p220ARCMSVapo 14 and 15 293 cells. In one instance, in clone 15-3, an additional deleted version of p220ARCMSVapo 15 was also observed, believed to represent a deletion which occurred shortly after transfection.

To date, we have performed such analysis on 10 clones and 2 populations of drug-resistant 293 cells produced by p220SMneo and on 3 clones and 2 populations produced by p220ARCMSVapo 14 and 15. In all instances, unrearranged plasmid could be rescued from the mammalian cells even after two months in culture. Moreover, in 15 out of 17 drug resistant cell lines tested, only unrearranged plasmid was observed. For one of the 293 cell clones, referred to as neoC,, we have retrieved the p220SMneo plasmid three months after the establishment of the clone and examined the plasmid structure from 36 transformed bacterial colonies. In each case only unrearranged plasmid was observed. This result indicates that the AAV/EBV chimeric vectors can be stably maintained in 293 cells for a period of three months.

The above data are consistent with plasmid maintenance of the chimeric AAV/EBV vectors. In this situation, the chimeric plasmid replicates along with the host chromosome, presumably using the oriP region of EBV as its origin of replication.

EXAMPLE 4

Production of Recombinant AAV virus

In order to determine whether a switch to lytic AAV replication would ensue if the appropriate AAV helper factors were supplied, we performed the following experiment. Human 293 cells containing AAV/EBV chimeric vectors were plated out 2 days before virus generation into fresh medium lacking hygromycin B. These cells were seeded into cultures such that on the day of virus production, the cells were approximately 25-40% confluent on 100-mm culture dishes. To produce recombinant virus, these cells were infected with adenovirus 2 stocks (moi of 1-5) for 2-4 hours. The cells were then transfected with 20 g p Bal using calcium phosphate mediated coprecipitation (Wigler, M. R., et al., "Transformation of Mammalian Cells with Genes From Procaryotes and Eukaryotes," Cell 16:777-785). The next day the medium was withdrawn and replaced with 5 ml of fresh medium lacking hygromycin B. Two days later, the cytopathic effect of adenovirus was evident, and recombinant AAV virus stock were harvested.

To harvest virus, the cells and medium were collected, and the cells were completely lysed by two 1-sec pulses of sonication. The viral stock was cleared of cellular debris by centrifugation and adenovirus was inactivated by heating the stock at 56° C. for one hour. Before use, the stock was filtered through a 1 micron cellulose acetate membrane.

Small molecular weight DNA was collected from cells using the procedure of Hirt as described in (1967) "Selective Extraction of Polyoma DNA From Infected Mouse Cultures," J. Mol. Biol. 126:275-288. This DNA was purified by treating the Hirt lysate with 10 g/ml proteinase K followed by sequential extractions with phenol and phenol: chloroform: isoamyl alcohol (25:24:1). The purified DNA was then concentrated by ethanol precipitation and used as described. For Southern blots, the DNA was run on 0.8% agarose gels and blotted onto nylon membranes (Hybond N+; Amersham). Blots were probed with DNA fragments labeled by the random priming method (Pharmacia, Piscataway, N.J.). After aqueous hybridization at 65° C., the filters were washed at 65° C. with solutions of increasing stringency concluding with 0.1×SSC (15 mM NaCl, 1.5 mM sodium citrate ph 7.0,)+1.0% SDS. Autoradiogram were produced by exposure to X-ray film (type XAR; Eastman Kodak Co. Rochester, N.Y.).

For the analysis of the episomal nature of chimeric AAV/EBV plasmids in 293 cells, small molecular weight DNA was isolated from cells using the Hirt procedure as described above and transformed into *E. coli* strain HB101. Small-scale preparations of plasmid were purified from 1 ml cultures of single bacterial colonies. Plasmid characterization was performed by restriction enzyme analysis.

When cells containing 220ARCMSVapo14 or 15 plasmid were infected with adenovirus and transfected with p Bal, lytic replication of the AAV construct began. This event was evidenced by the appearance of a 2.8 kb band which hybridizes to an apoAl probe. This 2.8 kb band is the correct size for the recombinant ARCMSVapo genome cloned into p220ARCMSVapo14 and 15. Also visible were a ladder of faint bands starting at 5.6 kb. These bands represent multimers of the recombinant AAV genome which are known to be intermediates in AAV replication.

The appearance of the 2.8-kb recombinant AAV genome is completely dependent on the presence of wild type AAV helper functions. If these same cells were simply infected with adenovirus or infected with adenovirus and transfected with the rep deletion mutant pSCcap, no ARCMSVapo replication was observed. Moreover, the amplication of the recombinant AAV construct was dependent on the presence of the AAV/EBV chimeric plasmid. Parental 293 cells which lack the AAV/EBV chimeric vector showed no ARCMSVapo amplification even in the presence of both wild type AAV functions. To date, we have tested a total of six p220ARCMSVapo14 and eleven p220ARCMSVapo15 clones. In every instance, replication of the recombinant AAV construct occurred when the cells were supplied with adenovirus and wild type AAV functions. Moreover, such amplification did not depend on the orientation of the recombinant AAV construct in the EBV vector. Both orientations led to similar levels of ARCMSVapo amplification.

Lytic replication of the recombinant AAV construct can also be initiated in cell clones containing p220SMneo. Again, replication of the recombinant AAV construct was dependent on the simultaneous presence of adenovirus and wild type AAV functions. p220SMneo cell clones which have been simply infected with adenovirus do no contain sequences of the recombinant ASMneo size. Similar results were observed if these cells are infected with adenovirus and transfected with the rep mutant pSCcap. However, if these adenovirus infected clones are provided both the rep and capsid functions of AAV from p Bal, lytic replication of ASMneo occurs as detected by the appearance of a 4.1-kb band which hybridizes with the neomycin phosphotransferase gene. This 4.1-kb fragment is the expected size of the recombinant ASMneo genome. Again, 293 cells which do not contain the chimeric plasmid do not show the appearance of the 4.1-kb band under any circumstances. Therefore, replication of a recombinant AAV vector can occur from the two different chimeric AAV/EBV plasmid types tested and indicates that this phenomenon is applicable to a wide variety of constructs.

EXAMPLE 5

Analysis of transfected cells for recombinational events

The AAV constructs in p220ARCMSVapo14, 15, and p220SMneo have all but 1350 bases of wild type AAV DNA deleted. They are defective for both the rep and capsid functions of AAV. The plasmid p Bal, which is used to supply the rep and capsid AAV functions, is wild type for all AAV sequences except for deletions of 121 bases in each 145 base terminal repeat. As a result, the AAV construct in p Bal is defective for the cis functions necessary for AAV viral replication. One important question in these studies was whether recombinational events occur during recombinant AAV replication to generate replicating wild type AAV genomes.

To answer this question, cell clones containing either p220ARCMSVapo14, 15, or p220SMneo were infected with adenovirus and transfected with p Bal. Forty-eight hours later, Hirt extracts of these transfectants were made and analyzed for the presence of recombinant and wild AAV sequences.

As outlined above, such treatment of the AAV/EBV chimeric vector cell clones induces amplification of the recombinant AAV construct as evidenced by the appearance of the appropriate recombinant genomes of 2.8 and 4.1 kb. When these same Southern blots were reprobed with the AAV capsid gene, no bands corresponding to the 4.7-kb, wild-type genome were observed. The only hybridizing sequences sometimes observed correspond to those from residual p Bal plasmid DNA remaining on the cells after transfection. Support for this conclusion comes from the observation that these residual super-coiled, nicked, and linear p Bal bands can also be observed after identical treatment of parental 293 cells. Therefore, during the greater than 10,000-fold amplification of the recombinant AAV construct, no detectable production of the wild type genome can be observed.

EXAMPLE 6

Analysis of recombinant AAV virus produced by the method of the invention.

Viral stocks produced from p220SMneo cell clones treated with both adenovirus and p Bal were tested for the presence of transducing recombinant ASMneo virus. In these experiments, K562 cells, from a human leukemia line, were exposed to such stocks and were subsequently selected for the presence of the neomycin phosphotransferase gene. Table 1 shows the results of three such experiments.

TABLE 1

| 220SMneo | Infection Efficiencies Produced by Recombinant AAV Stocks. | | |
|---|---|---|---|
| | % of K562 Cells Infected | | |
| Cell Line | EXPT 1 | EXPT 2 | EXPT 3 |
| clone1 | 0.04 | — | — |
| clone2 | — | 0.03 | — |
| clone3 | 0.5 | — | — |
| clone4 | 0.7 | 1.0 | — |
| clone5 | 0.0 | 0.0 | — |
| population1 | 0.8 | 0.0 | — |
| cloneA' | — | — | 0.15 |
| cloneB' | — | — | 0.10 |
| cloneC' | — | 0.05 | — |
| cloneD' | — | — | 0.10 |
| population1' | — | — | 1.0 |

Eleven of the cell lines tested produced recombinant AAV virus which was capable of infecting K562 cells and stably producing G418 resistant K562 clones. Infection efficiencies varied somewhat from experiment to experiment ranging from 0.0.04 to 1.0%. There was also some variability in the viral titers of stocks produced from the various p220SMneo cell clones. For instance, recombinant virus stocks produced from cell lines 220SMneo4 routinely produced higher infection efficiencies than those from the other cell clones.

Recombinant virus produced from p220SMneo and p220ARCMSVapo15 clones are also capable of coinfection. K562 cells were coinfected with ASMneo and ARCMSVapo stocks that were produced as described above. G418 resistant clones were selected, pooled, and screened for the secretion of apolipoprotein Al. In one such experiment, these and control K562 cells were labeled with 35S-methionine, and the cell culture supernatant was immunoprecipitated with a polyclonal anti-apoAl antibody. Briefly, coinfected cells were labeled for 4 days in standard medium containing 200 Ci 35S-methionine. At this point, the culture medium was cleared of cells by centrifugation and incubated with 100 l of protein-A-conjugated agarose beads (Repligen) which had been previously coated for 3 hours with an excess of anti-human apolipoprotein Al rabbit antiserum (Boehringer Manheim). The cell culture medium bead mixture was incubated overnight at 37° C. using gentle rotation. The following morning, the beads were collected and washed two times by centrifugation. Bound proteins were released using Laemmli sample buffer and analyzed on 15% SDS/PAGE gels according to the method of Laemmli, U. K., *Nature* (1970) 227:680–685. Cell culture proteins which were immunoprecipitated were visualized by autoradiography.

Analysis of the immunoprecipitates indicates that Apolipoprotein Al was secreted from the cells coinfected with the two viral stocks. Control K562 cells did not secrete this protein. These combined experiments indicated that recombinant AAV virus produced by this simplified method can be used to easily transduce one or two genes into single cells. In the context of these vectors, the transduced genes can be properly expressed and their proteins appropriately targeted to various cell compartments.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A recombinant plasmid vector, comprising in the order given in the 5'-3' direction:
   an Epstein Barr nuclear antigen (EBNA) gene, an Epstein Barr virus (EBV) latent origin of replication (oriP), and a recombinant adeno-associated virus (AAV) transducing vector comprising exogenous genetic material and lacking a functional AAV rep gene.

2. The vector of claim 1, wherein said plasmid vector comprises a detectible genetic marker.

3. The vector of claim 2, wherein said genetic marker is an antibiotic resistance gene.

4. The vector of claim 3, wherein said antibiotic resistance gene is located in said AAV vector.

5. The vector of claim 3, wherein said antibiotic resistance gene is located in said plasmid vector outside said AAV vector.

6. The vector of claim 1, wherein at least two genetic markers are present in said plasmid vector, an antibiotic resistance gene in said AAV vector and a second genetic marker located in said plasmid vector outside said AAV vector.

7. The vector of claim 1, wherein said AAV vector further lacks a functioning structural capsid gene segment.

8. The vector of claim 1, wherein said recombinant AAV vector comprises a selectable marker gene and two or more exogenous genes.

9. A method for producing AAV vectors, which comprises:
   cloning a preformed AAV transducing vector containing exogenous genetic material into an EBV plasmid, wherein said EBV plasmid comprises an EBNA gene, an oriP DNA fragment, and a detectible genetic marker;
   transfecting a host cell line with the resulting EBV-/AAV chimeric plasmid to produce a transfected cell line;
   growing said transfected cell line in a cell growth medium;
   contacting said transfected cell line with adenovirus and wild-type adeno-associated virus helper functions; and
   isolating said AAV vector from said cell growth medium.

* * * * *